United States Patent [19]

Danieli

[11] Patent Number: 5,152,280
[45] Date of Patent: Oct. 6, 1992

[54] BONE SUPPORT DEVICE

[75] Inventor: Guido Danieli, Milan, Italy

[73] Assignee: Confida S.a.S, Milan, Italy

[21] Appl. No.: 573,184

[22] PCT Filed: Dec. 20, 1989

[86] PCT No.: PCT/EP89/01581
§ 371 Date: Aug. 23, 1990
§ 102(e) Date: Aug. 23, 1990

[87] PCT Pub. No.: WO90/07305
PCT Pub. Date: Jul. 12, 1990

[30] Foreign Application Priority Data

Jan. 4, 1989 [IT] Italy ............... 19010 A/89

[51] Int. Cl.⁵ .......................................... A61B 17/60
[52] U.S. Cl. ............................... 128/54; 128/57
[58] Field of Search .......................... 606/54-59

[56] References Cited

U.S. PATENT DOCUMENTS

| | | | |
|---|---|---|---|
| 2,391,537 | 12/1945 | Anderson | 606/54 |
| 4,135,505 | 1/1979 | Day | 606/54 |
| 4,273,116 | 6/1981 | Chiquet | 606/54 |
| 4,312,336 | 1/1982 | Danieletto et al. | 606/59 X |
| 4,483,334 | 11/1984 | Murray | 606/54 X |
| 4,620,533 | 11/1986 | Mears | 606/54 |
| 4,621,627 | 11/1986 | DeBastianni et al. | 606/54 |
| 4,714,076 | 12/1987 | Compte et al. | 606/54 |
| 4,745,913 | 5/1988 | Castaman et al. | 606/54 |
| 4,895,141 | 1/1990 | Koeneman et al. | 606/54 |
| 4,944,743 | 7/1990 | Gotzen et al. | 606/59 X |
| 4,988,349 | 1/1991 | Pennig | 606/59 X |

FOREIGN PATENT DOCUMENTS

| | | |
|---|---|---|
| 0153546 | 3/1984 | European Pat. Off. |
| 2832283 | 2/1979 | Fed. Rep. of Germany |
| 3543042 | 6/1987 | Fed. Rep. of Germany |
| 2718515 | 10/1987 | Fed. Rep. of Germany |
| 3701533 | 8/1988 | Fed. Rep. of Germany |
| 8602822 | 5/1986 | World Int. Prop. O. |

Primary Examiner—Robert A. Hafer
Assistant Examiner—Kevin G. Rooney
Attorney, Agent, or Firm—Wolf, Greenfield & Sacks

[57] ABSTRACT

The present invention relates to a bone support device for supporting fragments of bone, in particular of fractured bones of the human body. The device includes a first member adapted to be connected to a bone fragment, a second member adapted to be connected to another bone fragment, and an adjustable articulated central body connected to the first and second members. The device allows to adjust the relative position of the two bones.

29 Claims, 2 Drawing Sheets

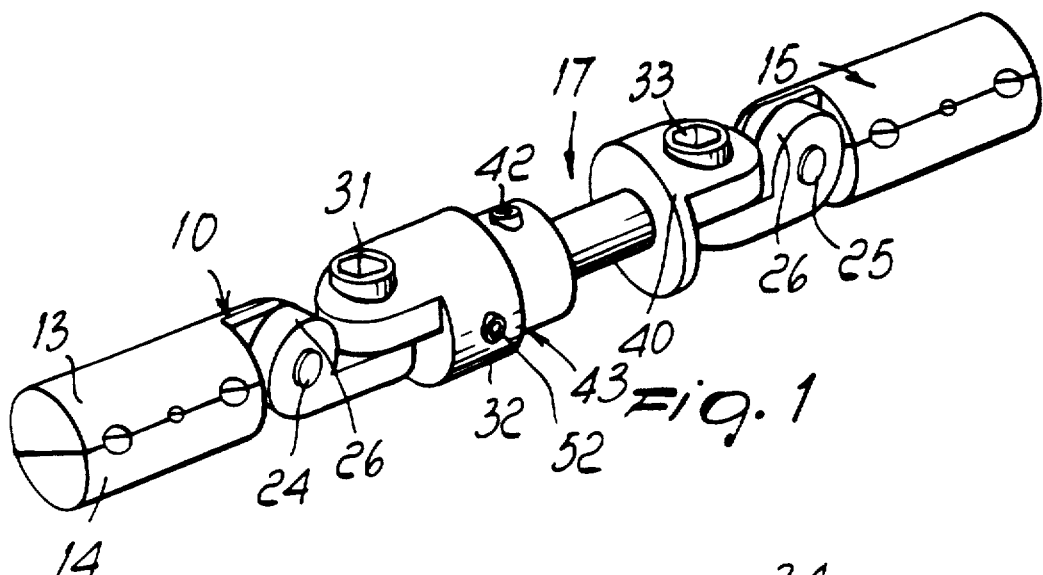
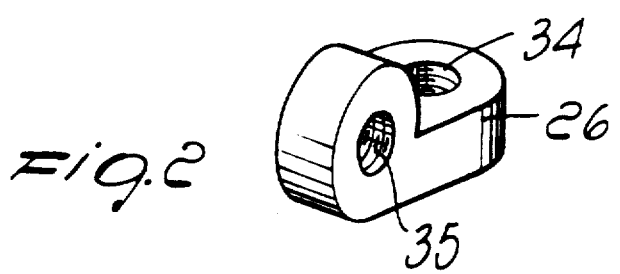
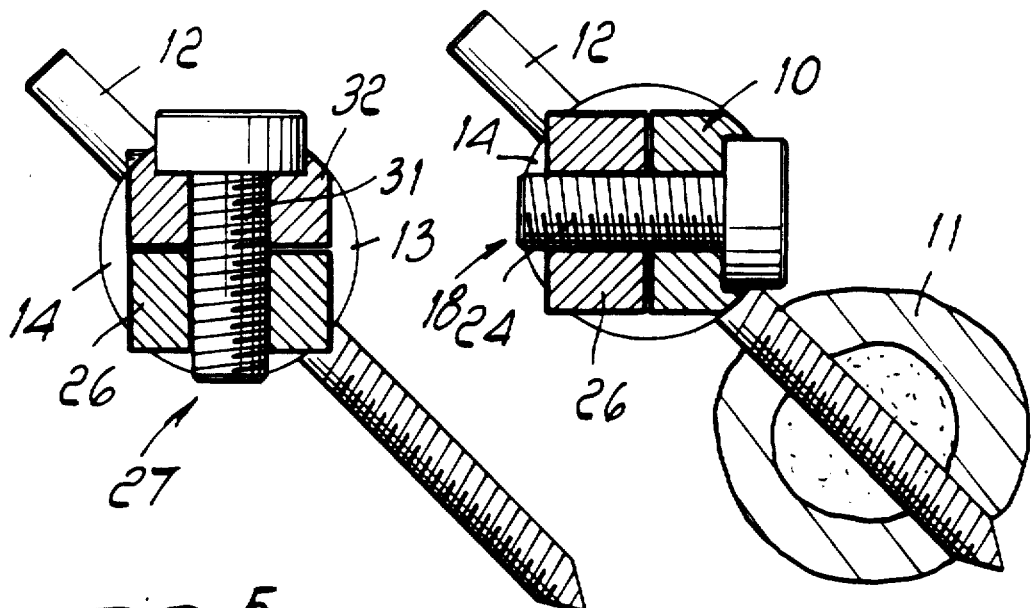

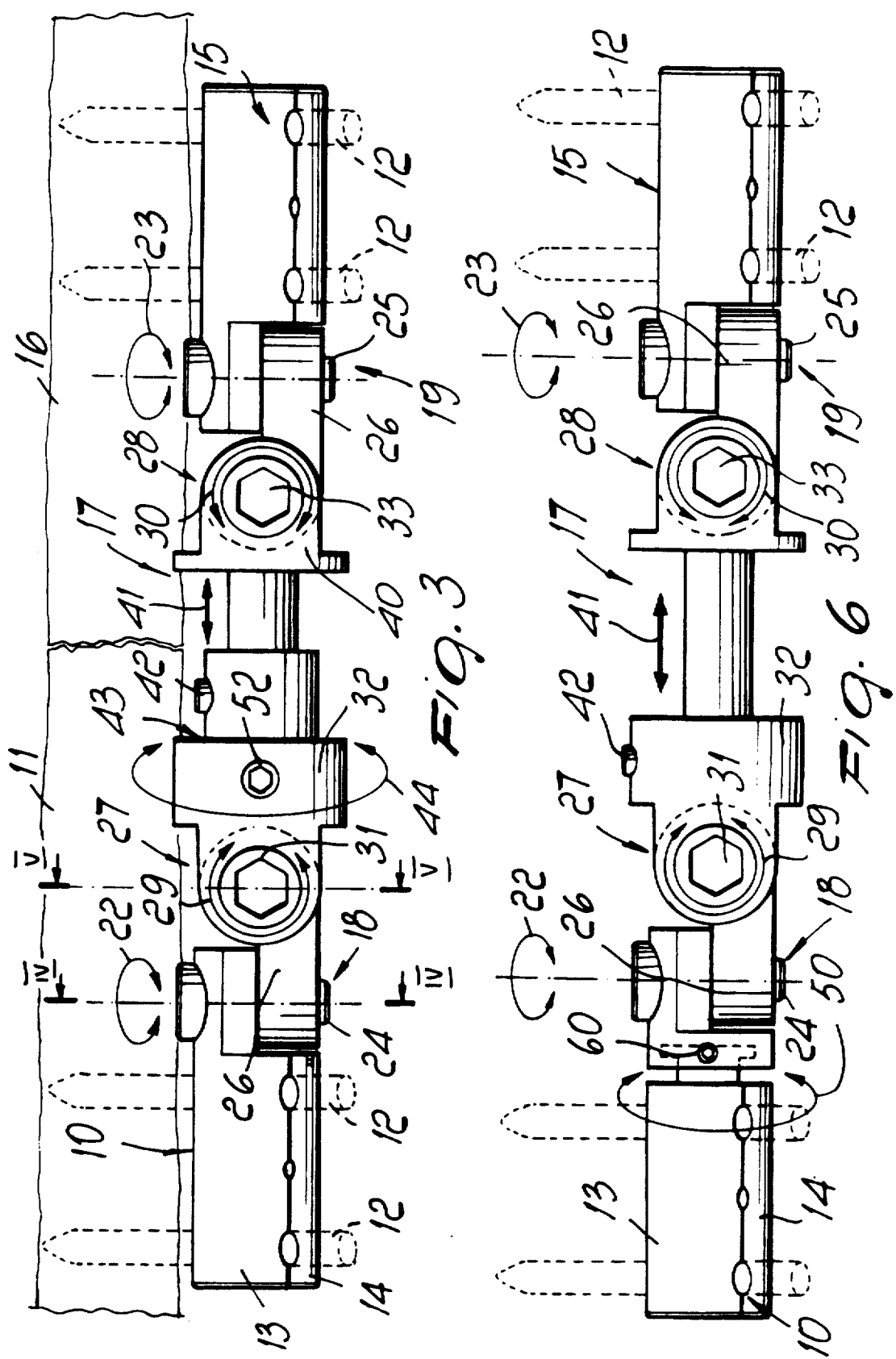

BONE SUPPORT DEVICE

TECHNICAL FIELD

The present invention relates to a bone support device for supporting fragments of bone, in particular of fractured bones of the human body. Said fractured bones must be kept in a presettable relative position, so as to allow the natural process of knitting of the bone fragments in the best possible manner.

More in particular, the device comprises a first member adapted to be rigidly connected to the first of said bone fragments and a second member adapted to be rigidly connected to the second of said bone fragments. More in particular, the rigid couplings are provided by means of screws which penetrate in adapted holes provided in the bone fragments. The device furthermore comprises an adjustable articulated central body which is connected to the first member and to the second member. The articulated central body allows to adjust the relative position of the first member with respect to the second member and to rigidly lock this relative position at a point which is particularly suitable to obtain the perfect knitting of the bone fragments.

This relative locked position can in certain cases be released during the healing process to allow a single degree of freedom of release. This single degree of freedom of release allows the translatory motion of the first member with respect to the second member which is directed substantially along the axis of the fractured bone. It has in fact been observed that this single degree of freedom of release allows a "dynamic" knitting of the bone fragments which produces a greater strength of the knitted bone. It has in fact been observed that "static" knitting, provided when the two bone fragments are rigidly locked in their relative position, provides a more fragile final knitting.

In particular, the relative arrangement of the two fractured bone fragments and therefore the corresponding relative arrangement of the first and second members are performed by a surgeon, who can control the position of the two bone fragments by virtue of detection means such as for example X-rays. Since said detection means allow to detect the position of the two bone fragments on a single plane, at least two different detections, taken along two different planes of exposure to radiation, are required, so as to verify that the position of the two bone fragments is correct in the three spatial dimensions. Said two detections can be performed on two planes which are inclined at 90° with respect to one another.

The above is in summary the main field of industrial application of the invention; said field, however, does not constitute a limitation of the scope thereof, since the device according to the invention, in particular as described and claimed hereinafter, can be advantageously used in any other equivalent field in which fractured bone fragments must be knitted, keeping them in a presettable relative position.

BACKGROUND ART

Devices of this kind are known and are described for example in the following patents: U.S. Pat. No. 4,312,336; U.S. Pat. No. Re. 31,809; DE 2718515; DE 3543042; DE 3701533; in said devices, the central body is connected to the first member by means of a spherical hinge and to the second member by means of another spherical hinge. Said spherical hinges can be locked in such a manner as to lock the relative position of the first member with respect to the second member.

However, said known devices entail some problems: first of all, the need to perform two detections, for example on two planes orientated at 90° with respect to one another, entails difficult problems for the physician, since the position defined on one plane is unavoidably modified when an attempt is made to adjust the position on the second detection plane. This entails the problem of having to perform multiple successive checks between the two detection planes, so as to ensure that the position is correct. This problem is increased by the fact that the radiation useful for performing the checks, such as for example X rays, are harmful for the physician and for the patient.

Other devices of this kind are known and are described for example in the European patent No. 153546 and in the PCT patent no. VO 86/02822; in said devices, each screw is supported by a spherical hinge. Such devices have the same disadvantages as the above described known devices, and furthermore have a very limited articulation, so that if the holes for inserting the screws in the two bone fragments are not performed with great precision there is the risk of no longer being able to compose the fracture in the correct relative position of said two bone fragements.

Another device of this kind is also known and is described in the German patent application no. 2832283; in said device, the central body comprises a series of hinges. This device entails the same problems described in the preceding cases and in practice it has been found to be very complicated and difficult to use for the physician.

DISCLOSURE OF THE INVENTION

The aim of the present invention is therefore to eliminate all the above described disadvantages.

An object of the invention is to allow to obtain the relative position of the fractured bone fragments with great precision and speed.

Another object of the invention is to allow a particularly simple and intuitive "friendly" use which can be learned without trouble by orthopedists without requiring particular specific training.

Not least object of the invention is to minimize the time of exposure to harmful radiation during the relative positioning of the two fractured bone fragments.

This aim, these objects and others are achieved by the device according to the invention, which comprises a first member adapted to be rigidly connected to the first bone fragment, a second member adapted to be rigidly connected to the second bone fragment, and an adjustable articulated central body connected to said first member and to said second member, said articulated central body allowing to adjust the position of said first member with respect to said second member and to rigidly lock said position; characterized in that said articulated central body comprises:

first articulation means which allow the rotation of said first member and of said second member on a first articulation plane;

second articulation means which allow the rotation of said first member and of said second member on a second articulation plane;

said first articulation means and said second articulation means being adjustable and lockable independently of one another, so that the rotations of said first member and of said second member on said first articulation plane and on said second articulation plane can be adjusted independently for each of said articulation planes and the adjustment of said first articulation plane does not interfere with the adjustment of said second articulation plane and vice versa.

BRIEF DESCRIPTION OF THE DRAWINGS

Further characteristics and advantages of the invention will become apparent from the description of two preferred but not exclusive embodiments of the device, illustrated only by way of non-limitative example in the accompanying drawings, wherein:

FIG. 1 is a perspective view of the first embodiment of the invention;

FIG. 2 is a perspective view of an enlarged detail of FIG. 1;

FIG. 3 is a plan view of the device of FIG. 1;

FIG. 4 is a sectional view taken along the plane IV—IV of FIG. 3;

FIG. 5 is a sectional view taken along the plane V—V of FIG. 3, and

FIG. 6 is a plan view of the device according to the second embodiment of the invention.

WAYS OF CARRYING OUT THE INVENTION

With reference to FIGS. 1 to 6, the device according to the invention comprises a first member 10 adapted to be connected to the first bone fragment 11. In particular, the rigid coupling between the first member 10 and the bone fragment 11 is provided by means of screws 12 which penetrate in adapted holes provided on the bone fragment 11. In order to lock the screws, the first member 10 is composed of two elements 13 and 14 which can be mutually coupled so as to lock the screws in position. The second member 15 is shaped similarly to the first member 10, so that it can be rigidly connected to the second bone fragment 16.

The articulated central body 17 connects the first member 10 to the second member 15 and comprises first articulation means 18 and 19 and second articulation means 27 and 28. Said first articulation means 18 and 19 allow the rotation of the first member 10 with respect to the second member 15 on a first articulation plane schematically represented by the arrows 22 and 23. In particular, said first articulation plane is perpendicular to the axis of the first pair of hinges 18 and 19.

With particular reference to FIG. 4, the hinge 18 is illustrated; said hinge is formed by the bolt 24 which engages the first member 10 and the connecting body 26. The second hinge 19 of the first pair of hinges is formed in a similar manner. The configuration of the connecting body 26 is illustrated in detail with particular reference to FIG. 2. The first articulation means 18, 19 are adjustable independently of the other articulation means simply by acting on the bolts 24 and 25. The simple locking of said bolts allows to lock the first articulation means and therefore to adjust the position of the first member 10 with respect to the second member 15 on the first articulation plane defined by the arrows 22 and 23.

With reference to FIGS. 1 to 6, the second articulation means 27 and 28 comprise the second pair of hinges 27 and 28 which allows to adjust the rotation of the first member 10 with respect to the second member 15 about a second articulation plane defined in particular by the arrows 29 and 30. The hinge 27 is illustrated with particular reference to FIG. 5, wherein the bolt 31 which engages the connecting body 26 and the element 32 is illustrated. The second hinge 28 of the second pair of hinges is configured in a similar manner.

The second articulation means 27 and 28 are adjustable independently of the first articulation means 18 and 19 simply by acting on the bolts 31 and 33, which can be easily tightened so as to lock the position of the first member 10 with respect to the second member 15 in the second articulation plane.

With reference to FIGS. 1 to 6, the first articulation plane defined by the arrows 22 and 23 is inclined at 90° with respect to the second articulation plane defined by the arrows 29 and 30. Said 90° inclination is determined by the configuration of the connecting bodies 26 which have connecting holes 34 and 35 the axes whereof are inclined at 90°, as illustrated in particular in FIG. 2.

The axes of the screws 12 adapted to be inserted in the bone fragments are preferably offset so as to be inclined with respect to the first articulation plane 22, 23 and to the second articulation plane 29, 30. More preferably, said inclination is at 45°. In particular, said 45°-inclination is allowed by the inclination of the supporting holes of the bolt 24 with respect to the supporting holes of the screws 12, as provided on the first member 10. This is similarly true for the inclination of the supporting hole of the bolt 25 and of the screws 12 of the second member 15. Said holes are mutually offset by 45°.

Each of the hinges 18, 19 of the first pair of hinges and each of the hinges 27 and 28 of the second pair of hinges has a single degree of freedom, indicated respectively by the rotation of the arrows 22, 23, 29 and 30.

Each hinge 27 and 28 of the second pair of hinges is respectively connected to the first articulation means 18 and 19 by means of the connecting bodies 26.

The elements 32 and 40 of the second pair of hinges are connected to one another by means of third articulation means, represented by the arrow 41, which allow the relative approach and spacing of the axes of the second pair of hinges. In particular, the third articulation means comprise a translatory joint which can be locked by means of the bolt 42. The axial sliding 41 allows a dynamic knitting of the fractured bones, allowing an axial movement of the two bone fragments 11 and 16.

With reference to FIGS. 1 to 5, according to the first embodiment of the invention fourth articulation means 43 are provided which allow the rotation of the first member 10 with respect to the second member 15 in the direction indicated by the arrow 44. Said fourth articulation means are in practice used only for slight rotations of the first member with respect to the second member to compensate imprecisions due to the insertion of the screws in the bone fragments 11 and 16. The arrow 44 indicates the rotation about an axis of rotation which is substantially parallel to the axis of the bone fragments. In particular, the fourth articulation means mutually connect the elements 32 and 40 of the second pair of hinges 27 and 28. According to this first embodiment, the first articulation plane and the second articulation plane are defined with the approximation due to the rotation allowed by the fourth articulation means. Said rotation in fact tends to offset the axes of the hinges which are proximate to the first member 10 with respect to the axes of the hinges which are proximate to the second member 15. However, since said rotation due to the fourth articulation means is in practice always very small, the resulting approximation is sufficient in practice.

With reference to FIG. 6, said figure illustrates a second embodiment of the invention which is differentiated from the first embodiment only for the position of the fourth articulation means, which according to said second embodiment connect the first member 10 to the first articulation means and in particular to the hinge 18. In this case, too, the fourth articulation means allow the rotation of the first member 10 with respect to the second member 15 about an axis which is substantially parallel to the axis of the bone fragments 11 and 16; said rotation is indicated in particular by the arrow 50. According to this embodiment, the first articulation plane and the second articulation plane are defined with maximum precision, since the fourth articulation means do not affect the relative position of the axes of rotation of the hinges of the first articulation means and of the second articulation means.

According to both embodiments, the central articulated body 17 has six degrees of freedom which are represented by the arrows 22, 29, 44 or 50, 41, 30 and 23 and are individually lockable respectively by means of the bolts 24, 31, 52 or 60, 42, 33, 25.

I claim:

1. A bone support device for supporting bone fragments, comprising a first member adapted to be rigidly connected to the first of said bone fragments, a second member adapted to be rigidly connected to the second of said bone fragments, and an adjustable articulated central body connected to said first member and to said second member, said articulated central body facilitating the adjustment of the position of said first member with respect to said second member and facilitating the rigidly locking of said position; said articulated central body comprising:
    first articulation means which allow the rotation of said first member and of said second member on a first articulation plane;
    second articulation means which allow the rotation of said first member and of said second member on a second articulation plane;
    fourth articulation means to allow the rotation of said first member with respect to said second member about an axis which is substantially parallel to the axis of said bone fragments;
    said first articulation means and said second articulation means being adjustable and lockable independently of one another, so that the rotation of said first member and of said second member on said first articulation plane and on said second articulation plane can be independently adjusted for each of said articulation planes and the adjustment of said first articulation plane does not interfere with the adjustment of said second articulation plane and vice versa;
    said first articulation means comprising a first pair of hinges, each hinge allowing a single degree of freedom of rotation, one hinge being connected to said first member, the other being connected to said second member;
    said second articulation means comprising a second pair of hinges, each hinge of said second pair of hinges having a single degree of freedom of rotation and being connected directly to said first articulation means;
    said fourth articulation means mutually connecting the elements of said second pair of hinges.

2. Device according to claim 1, wherein said first articulation plane is inclined at 90° with respect to said second articulation plane.

3. Device according to claim 1, wherein said first member and said second member support screws adapted to be inserted in said bone fragments, the axes of each of said screws being offset with respect to said first articulation plane and to said second articulation plane.

4. Device according to claim 3, wherein said axes of said screws are inclined at 45° with respect to said first articulation plane and to said second articulation plane.

5. Device according to claim 1, wherein the axis of rotation of each hinge of said first pair of hinges is inclined at 45° with respect to the axis of said screws.

6. Device according to claim 1, wherein the axes of rotation of said first pair of hinges and of said second pair of hinges are inclined at 90° with respect to one another.

7. Device according to claim 1, wherein the elements of said second pair of hinges are mutually connected by means of third articulation means, said third articulation means allowing the relative approach and spacing of the axes of said second pair of hinges.

8. Device according to claim 7, wherein said third articulation means comprise a translatory joint.

9. A bone support device for supporting bone fragments, comprising a first member adapted to be rigidly connected to the first of said bone fragments, a second member adapted to be rigidly connected to the second of said bone fragments, and an adjustable articulated central body connected to said first member and to said second member, said articulated central body facilitating the adjustment of the position of said first member with respect to said second member and facilitating the rigid locking of said position; said articulated central body comprising:
    first articulation means which allow the rotation of said first member and of said second member on a first articulation plane;
    second articulation means which allow the rotation of said first member and of said second member on a first articulation plane; second articulation means which allow the rotation of said first member and of said second member on a second articulation plane;
    fourth articulation means to allow the rotation of said first member with respect to said second member about an axis which is substantially parallel to the axis of said bone fragments;
    said first articulation means and said second articulation means being adjustable and lockable independently of one another, so that the rotation of said first member and of said second member on said first articulation plane and on said second articulation plane can be independently adjusted for each of said articulation planes and the adjustment of said first articulation plane does not interfere with the adjustment of said second articulation plane and vice versa;
    said first articulation means comprising a first pair of hinges, each hinge allowing a single degree of freedom of rotation, one hinge being connected to said first member, the other being connected to said second member;
    said second articulation means comprising a second pair of hinges, each hinge of said second pair of hinges having a single degree of freedom of rotation and being connected directly to said first articulation means;

said fourth articulation means mutually connecting said first member and said first articulation means.

10. Device according to claim 9, wherein said first articulation plane is inclinded at 90° with respect to said second articulation plane.

11. Device according to claim 9, wherein said first member and said second member support screws adapted to be inserted in said bone fragments, the axes of each of said screws being offset with respect to said first articulation plane and with respect to said second articulation plane.

12. Device according to claim 11, wherein said axes of said screws are inclined at 45° with respect to said first articulation plane an to said second articulation plane.

13. Device according to claim 9, wherein the axis of rotation of each hinge of said first pair of hinges is inclined at 45° with respect to the axis of said screws.

14. Device according to claim 9, wherein the axes of rotation of said first pair of hinges and of said second pair of hinges are inclined at 90° with respect to one another.

15. Device according to claim 9, wherein the elements of said second pair of hinges are mutually connected by means of third articulation means, said third articulation means allowing the relative approach and spacing of the axes of said second pair of hinges.

16. Device according to claim 15, wherein said third articulation means comprise a translatory joint.

17. A bone support device for supporting bone fragments, comprising a first member adapted to be rigidly connected to the first of said bone fragments, a second member adapted to be rigidly connected to the second of said bone fragments, and an adjustable articulated central body connected to said first member and to said second member, said articulated central body facilitating the adjustment of the position of said first member with respect to said second member and facilitating the rigid locking of said position; said articulated central body comprising:

first articulation means which allow the rotation of said first member and of said second member on a first articulation plane;

second articulation means which allow the rotation of said first member and of said second member on a second articulation plane;

said first articulation means and said second articulation means being adjustable and lockable independently of one another, so that the rotation of said first member and of said second member on said first articulation plane and on said second articulation plane can be independently adjusted for each of said articulation planes and the adjustment of said first articulation plane does not interfere with the adjustment of said second articulation plane and vice versa;

said articulated central body comprising six individually lockable degrees of freedom.

18. Device according to claim 17, wherein said first articulation plane is inclined at 90° with respect to said second articulation plane.

19. Device according to claim 17, wherein said first member and said second member support screws adapted to be inserted in said bone fragments, the axes of each of said screws being offset with respect to said first articulation plane and with respect to said second articulation plane.

20. Device according to claim 19, wherein said axes of said screws are inclined at 45° with respect to said first articulation plane and to said second articulation plane.

21. Device according to claim 17, wherein said first articulation means comprise a first pair of hinges, each hinge allowing a single degree of freedom of rotation, one hinge being connected to said first member, the other being connected to said second member.

22. Device according to claim 21, wherein the axis of rotation of each hinge of said first pair of hinges is inclined at 45° with respect to the axis of said screws.

23. Device according to claim 21, wherein said second articulation means comprise a second pair of hinges, each hinge of said second pair of hinges having a single degree of freedom of rotation and being connected directly to said first articulation means.

24. Device according to claim 23, wherein the axes of rotation of said first pair of hinges and of said second pair of hinges are inclined at 90° with respect to one another.

25. Device according to claim 23, wherein the elements of said second pair of hinges are mutually connected by means of third articulation means, said third articulation means allowing the relative approach and spacing of the axes of said second pair of hinges.

26. Device according to claim 25, wherein said third articulation means comprise a translatory joint.

27. Device according to claim 23, wherein it comprises fourth articulation means to allow the rotation of said first member with respect to said second member about an axis which is substantially parallel to the axis of said bone fragments.

28. Device according to claim 27, wherein said fourth articulation means mutually connect the elements of said second pair of hinges.

29. Device according to claim 27, wherein said fourth articulation means mutually connect said first member and said first articulation means.

* * * * *